US009151854B2

(12) United States Patent
Han et al.

(10) Patent No.: US 9,151,854 B2
(45) Date of Patent: Oct. 6, 2015

(54) INFORMATION DETECTION APPARATUS, PHANTOM INFORMATION RECORDING APPARATUS AND OPERATION METHOD THEREOF

(71) Applicant: SAMSUNG ELECTRONICS CO., LTD., Suwon-si (KR)

(72) Inventors: Seok Min Han, Seongnam-si (KR); Dong Goo Kang, Suwon-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 255 days.

(21) Appl. No.: 13/955,643

(22) Filed: Jul. 31, 2013

(65) Prior Publication Data
US 2014/0037072 A1    Feb. 6, 2014

(30) Foreign Application Priority Data

Aug. 3, 2012    (KR) .................. 10-2012-0085028
Nov. 5, 2012    (KR) .................. 10-2012-0124058

(51) Int. Cl.
*G01N 23/06* (2006.01)
*G01T 7/00* (2006.01)
*A61B 6/00* (2006.01)
*G01N 23/087* (2006.01)

(52) U.S. Cl.
CPC ................. *G01T 7/005* (2013.01); *A61B 6/482* (2013.01); *A61B 6/583* (2013.01); *G01N 23/087* (2013.01); *G01N 2223/3035* (2013.01); *G01N 2223/423* (2013.01); *G01N 2223/612* (2013.01)

(58) Field of Classification Search
CPC ........ A61B 6/583; A61B 6/482; A61B 6/505; G06T 7/0012; G06T 2207/10116; G06T 7/005; G01N 23/087; G01N 2223/3035; G01N 2223/423
See application file for complete search history.

(56) References Cited

U.S. PATENT DOCUMENTS

| 6,148,057 A | 11/2000 | Urchuk et al. |
| 6,683,934 B1 | 1/2004 | Zhao et al. |
| 2006/0049358 A1 | 3/2006 | Oumi et al. |
| 2007/0189439 A1 | 8/2007 | Rinkel et al. |
| 2010/0098212 A1 | 4/2010 | Lang |

FOREIGN PATENT DOCUMENTS

| JP | 2011-067516 A | 4/2011 |
| KR | 10-2004-0048362 A | 6/2004 |
| KR | 10-2008-0007623 A | 1/2008 |
| KR | 10-2008-0071919 A | 8/2008 |
| KR | 10-2011-0058770 A | 6/2011 |

*Primary Examiner* — Courtney Thomas
(74) *Attorney, Agent, or Firm* — Sughrue Mion, PLLC

(57) ABSTRACT

A material information detection apparatus, a phantom information recording apparatus, and operation methods for the apparatuses are provided. The material information detection apparatus includes a database configured to store phantom information obtained by projecting a multi-energy X-ray on a phantom comprising a plurality of materials, an input device configured to receive a plurality of pieces of object information per energy level, the object information obtained by projecting a multi-energy X-ray on an analysis object, and a detector configured to detect information related to materials constituting the analysis object based on the phantom information and the plurality of pieces of object information per energy level.

20 Claims, 6 Drawing Sheets

INFORMATION DETECTION APPARATUS, PHANTOM INFORMATION RECORDING APPARATUS AND OPERATION METHOD THEREOF

CROSS-REFERENCE TO RELATED APPLICATION

This application claims the benefit of Korean Patent Application Nos. 10-2012-0085028, filed on Aug. 3, 2012, and 10-2012-0124058, filed on Nov. 5, 2012, in the Korean Intellectual Property Office, the disclosures of which are incorporated herein by reference in their entirety.

BACKGROUND

1. Field

One or more exemplary embodiments of the following description relate to a technology of detecting information on materials of an analysis object.

2. Description of the Related Art

For quantitative medical imaging or quantitative imaging using a multi-energy X-ray such as a dual energy X-ray, components of an object of imaging, in other words, an analysis object, should be calculated.

When imaging an analysis object such as, for example, human body using the multi-energy X-ray, a plurality of materials of the analysis object may be separated based on a combination according to a mixture ratio and a thickness, that is, a quantity, of the plurality of materials. Calibration refers to a process of finding relationships between an X-ray image and the combination based on the mixture ratio and the thickness of the plurality of materials.

To increase the accuracy of calibration with respect to a phantom including a plurality of materials, calibration should be performed with respect to all possible mixture ratios and thicknesses.

SUMMARY

According to exemplary embodiments, the foregoing and/or other aspects are achieved by providing a material information detection apparatus including a database configured to store phantom information obtained by projecting a multi-energy X-ray on a phantom comprising a plurality of materials, an input device configured to receive an input of a plurality of pieces of object information per energy level, the object information obtained by projecting a multi-energy X-ray on an analysis object, and a detector configured to detect information related to materials constituting the analysis object based on the phantom information and the plurality of pieces of object information per energy level.

According to exemplary embodiments, the foregoing and/or other aspects are also achieved by providing a phantom information recording apparatus including a generator configured to generate a phantom by mixing a plurality of materials, a detector configured to detect phantom information by projecting a multi-energy X-ray on the phantom, and a storage unit configured to store the phantom information.

According to exemplary embodiments, the foregoing and/or other aspects are also achieved by providing a method to be performed by a material information detection apparatus, the operation method including receiving a plurality of pieces of object information per energy level, the object information obtained by projecting a multi-energy X-ray on an analysis object, and detecting information related to materials constituting the analysis object based on phantom information and the plurality of pieces of object information per energy level, the phantom information being stored in a database of the material information detection apparatus, wherein the phantom information is information obtained by projecting the multi-energy X-ray on a phantom comprising a plurality of materials.

According to exemplary embodiments, the foregoing and/or other aspects are also achieved by providing a method to be performed by a phantom information recording apparatus, the method including generating a phantom by mixing a plurality of materials, detecting phantom information by projecting a multi-energy X-ray on the phantom, and storing the phantom information.

Additional aspects, features, and/or advantages of exemplary embodiments will be set forth in part in the description which follows and, in part, will be apparent from the description, or may be learned by practice of the disclosure.

BRIEF DESCRIPTION OF THE DRAWINGS

These and/or other aspects and advantages will become apparent and more readily appreciated from the following description of the exemplary embodiments, taken in conjunction with the accompanying drawings of which.

DETAILED DESCRIPTION

Figure 1:
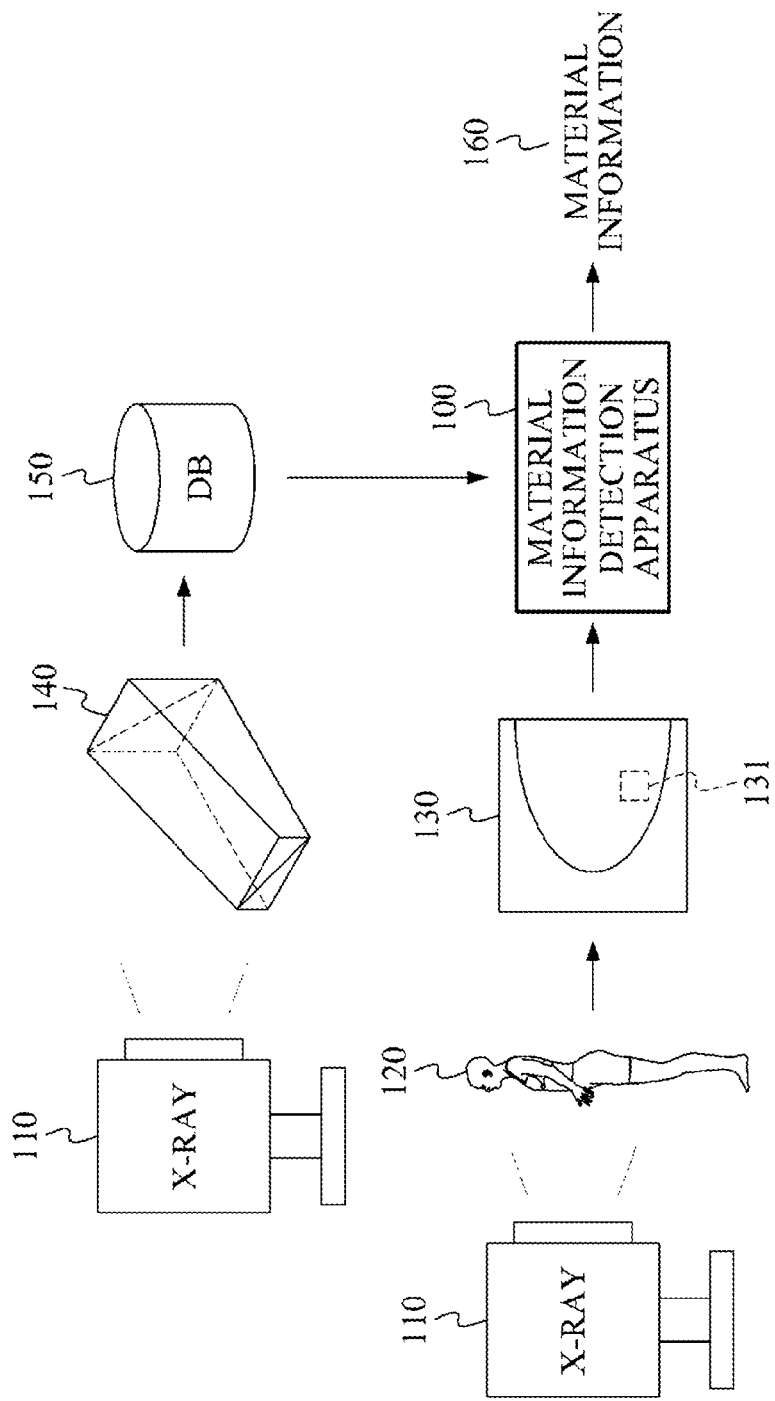
FIG. 1 illustrates an operation of a material information detection apparatus according to exemplary embodiments.

Reference will now be made in detail to exemplary embodiments, examples of which are illustrated in the accompanying drawings, wherein like reference numerals refer to the like elements throughout. However, the exemplary embodiments should be considered in a descriptive sense only and not for purposes of limitation.

Terms to be used below are defined based on their functions in the present exemplary embodiments and may vary according to users, user's intentions, or practices. Therefore, the definitions of the terms should be determined based on the entire specification.

FIG. 1 illustrates an operation of a material information detection apparatus 100 according to exemplary embodiments.

Referring to FIG. 1, the material information detection apparatus 100 may detect material information 160, that is, information on materials constituting an analysis object. For example, for quantitative medical imaging or quantitative imaging using a multi-energy X-ray 110 such as a dual energy X-ray, components of an object of imaging, that is, an analysis object, should be calculated. The material information detection apparatus 100 may detect information on the component materials of the analysis object, including information such as, for example, information related to components, a mixture ratio, a thickness, and the like.

The analysis object may be various types of objects, such as, for example, a person, an animal, an item, and the like. When the analysis object is a person 120, for example, the material information detection apparatus 100 may be input with an object image 130 obtained by projecting the multi-energy X-ray 110 on the person 120, and detect material information 160 which includes information on component materials of an analysis area 131, for example, a pixel, selected from the input object image 130, information on mixture ratios of the component materials, thicknesses of the respective component materials, and the like. Therefore, the material information detection apparatus 100 may be used to analyze whether a body part of a user has any diseases, by detecting the material information such as mixture ratios, thicknesses, and the like of materials constituting the body part.

The material information detection apparatus 100 may reference a database (DB) 150 storing phantom information so as to detect the material information 160 about the analysis object. The phantom information may be information obtained by projecting a multi-energy X-ray on a phantom 140 including a plurality of materials.

The material information detection apparatus 100 may detect the material information 160 related to the materials constituting the analysis object, by performing calibration. According to exemplary embodiments, calibration refers to an operation of finding relationships between the phantom information stored in the DB 150, such as the mixture ratios and thicknesses of the plurality of materials, and object information obtained by projecting the multi-energy X-ray 110 on an analysis object, for example, the person 120, by comparing the phantom information with the object information.

Furthermore, for more accurate calibration, the calibration may be performed with respect to all possible mixture ratios and thicknesses of a plurality of materials. The material information detection apparatus 100 may perform calibration using the phantom 140 including at least three materials. Therefore, the material information detection apparatus 100 may detect the material information 160 accurately even when an analysis object includes three or more component materials.

The phantom 140 may include at least one of a linear phantom and a non-linear phantom. Therefore, the phantom information stored in the DB 150 may be obtained by projecting a multi-energy X-ray on (1) the linear phantom, (2) the non-linear phantom, (3) a plurality of linear phantoms, (4) a plurality of non-linear phantoms, and (5) a combination of at least one linear phantom and at least one non-linear phantom.

According to exemplary embodiments, the linear phantom is designed such that thicknesses of a plurality of materials constituting the phantom linearly increase or decrease and mixture ratios of the plurality of materials linearly increase or decrease.

According to exemplary embodiments, the non-linear phantom is designed such that thicknesses of at least one of the plurality of materials constituting the phantom non-linearly increases or decreases or a mixture ratio of at least one of the plurality of materials non-linearly increases or decreases.

According to an aspect of exemplary embodiments, the phantom information stored in the DB used by the material information detection apparatus 100 may be information detected and stored by a phantom information recording apparatus. That is, the phantom information recording apparatus may generate a phantom by mixing a plurality of materials, detect the phantom information by projecting a multi-energy X-ray on the phantom, and store the phantom information in the DB. The phantom information recording apparatus according to exemplary embodiments will be described in detail later.

Hereinafter, one or more exemplary embodiments of the linear phantom and the non-linear phantom will be described with reference to FIGS. 2 and 3.

Figure 2:
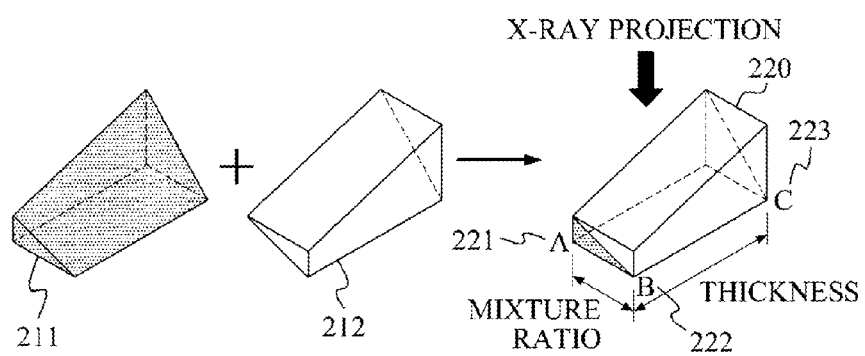
FIG. 2 illustrates a linear phantom according to exemplary embodiments.

FIG. 2 illustrates a linear phantom according to exemplary embodiments.

The linear phantom shown in FIG. 2 may, for example, include two materials. The materials of the linear phantom may be any one of an adipose tissue and a glandular tissue, although are not limited thereto.

According to exemplary embodiments, the linear phantom may be manufactured in a trapezoid shape 220. The linear phantom may be generated by the phantom information recording apparatus.

When manufactured in the trapezoid shape 220, thicknesses of a first material 211 and a second material 212 constituting the liner phantom may increase in a direction from a front surface B 222 to a rear surface C 223 of the linear phantom. For example, the thicknesses of the first material 211 and the second material 212 may be both about 5 cm at the front surface B 222 of the linear phantom. The thicknesses of the first material 211 and the second material 212 may linearly increase toward the rear surface C 223 and become about 10 cm at the rear surface 223 C. It is understood that the thicknesses are not limited to ranging from about 5 cm to about 10 cm, and may vary according to exemplary embodiments.

Since the first material 211 and the second material 212 are diagonally connected, the mixture ratio of the first material 211 and the second material 212 may linearly increase or decrease in a direction from a left surface A 221 to a right surface B 222. For example, the mixture ratio between the first material 211 and the second material 212 may be about 10:0 at the left surface A 221 of the linear phantom. The mixture ratio between the first material 211 and the second material 212 may linearly change toward the right surface B 222 and become about 0:10 at the right surface B 222.

The phantom information recording apparatus may obtain a phantom image by projecting a multi-energy X-ray on the linear phantom. According to exemplary embodiments, the phantom image may be obtained by projecting a multi-energy X-ray from above the linear phantom.

Figure 3:
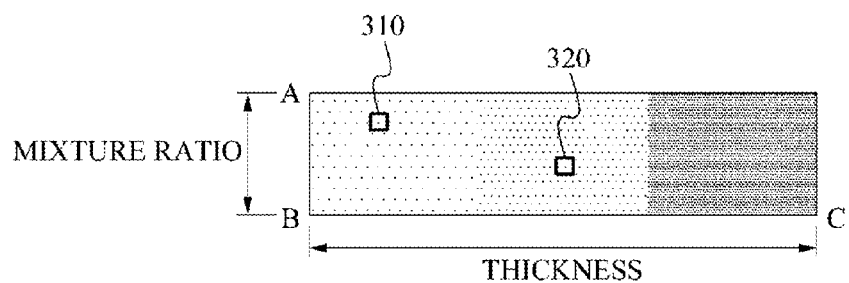
FIG. 3 illustrates a phantom image obtained by projecting a multi-energy X-ray on the linear phantom of FIG. 2.

FIG. 3 illustrates the phantom image obtained by projecting the multi-energy X-ray on the linear phantom of FIG. 2.

Since the phantom image is obtained by projecting a multi-energy X-ray from above the linear phantom of FIG. 2, the phantom image may be in a rectangular shape. A plurality of pixels of the phantom image may each include information such as the thicknesses and the mixture ratio of the first material 211 and the second material 212.

For example, a first pixel 310 may include information indicating a thickness of about 5.5 cm and a mixture ratio of about 8:2 of the first material 211 and the second material 212. A second pixel 320 may include information indicating a thickness of about 7.5 cm and a mixture ratio of about 5:5 of the first material 211 and the second material 212.

Figure 4:
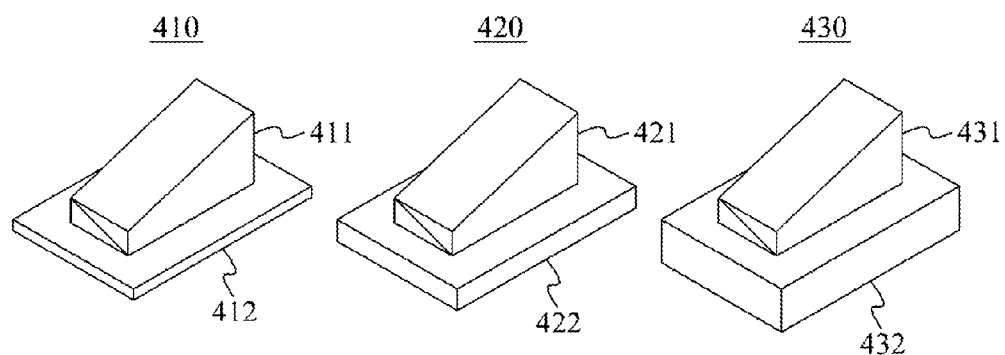
FIG. 4 illustrates non-linear phantoms according to other exemplary embodiments.

FIG. 4 illustrates non-linear phantoms according to other exemplary embodiments.

Non-linear phantoms 410, 420, and 430 shown in FIG. 4 may include three materials. Each of the materials constituting the non-linear phantoms 410, 420, and 430 may include at least one material selected from iodine (I), aluminum (Al), gold (Au), and calcium (Ca).

When the phantom includes at least three materials, the phantom may be non-linearly designed. That is, a thickness or a mixture ratio of at least one of the at least three materials may non-linearly increase or decrease.

The non-linear phantoms 410, 420, and 430 shown in FIG. 4 may be generated by generating a plurality of linear phantoms 411, 421, and 431 having the trapezoid shape as shown in FIG. 2 and then adding third materials 412, 422, and 432 having different thicknesses respectively to the plurality of linear phantoms 411, 421, and 431. The non-linear phantoms 410, 420, and 430 of FIG. 4 may be generated by the phantom information recording apparatus.

Therefore, in the non-linear phantoms 410, 420, and 430 of FIG. 4, the thicknesses and the mixture ratios of the first material and the second material may linearly increase or decrease. Alternatively, the thicknesses and the mixture ratios of the third materials 412, 422, and 432 may increase or decrease non-linearly, that is, discretely. For example, at least one of the thicknesses and the mixture ratios of the third materials 412, 422 and 432 may be constant.

For example, a thickness of the third material 412 may be about 2 cm in the first non-linear phantom 410, a thickness of the third material 422 may be about 5 cm in the second non-linear phantom 420, and a thickness of the third material 432 may be about 8 cm in the third non-linear phantom 430.

The phantom information recording apparatus may obtain the phantom image by projecting a multi-energy X-ray on the non-linear phantoms 410, 420, and 430 designed as aforementioned.

Hereinafter, a configuration of the phantom information recording apparatus according to exemplary embodiments will be described.

Figure 5:
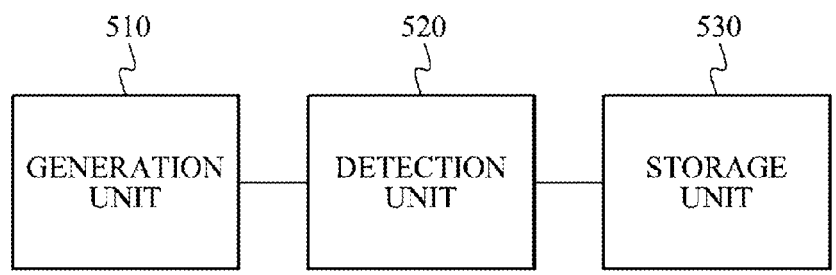
FIG. 5 illustrates a configuration of a phantom information recording apparatus according to exemplary embodiments.

FIG. 5 illustrates a configuration of a phantom information recording apparatus according to exemplary embodiments.

Referring to FIG. 5, the phantom information recording apparatus may include a generation unit 510 (e.g., generator), a detection unit 520 (e.g., detector), and a storage unit 530 (e.g., storage).

The generation unit 510 may generate a phantom by mixing a plurality of materials.

The detection unit 520 may detect phantom information by projecting a multi-energy X-ray on the phantom. The phantom information may include a phantom image formed by photographing the phantom using a multi-energy X-ray and information of component materials, such as a thickness and a mixture ratio, corresponding to positions of pixels of the phantom image.

The storage unit 530 may store the detected phantom information in a database (DB).

According to exemplary embodiments, the generation unit 510 may generate two linear phantoms as described with reference to FIG. 2.

In detail, the generation unit 510 may generate a first linear phantom by mixing a first material and a second material, such that thicknesses of the first material and the second material linearly increase or decrease and such that mixture ratios of the first material and the second material linearly increase or decrease.

In addition, the generation unit 510 may generate a second linear phantom by mixing a third material and a fourth material, such that thicknesses of the third material and the fourth material linearly increase or decrease and such that mixture ratios of the third material and the fourth material linearly increase or decrease.

Here, the first material, the second material, the third material, and the fourth material may each include at least one of an adipose tissue and a glandular tissue, or materials which are equivalent to an adipose or glandular tissue.

When the generation unit 510 thus generates two linear phantoms, the detection unit 520 may detect the phantom information by projecting a multi-energy X-ray on the first linear phantom and the second linear phantom.

According to other exemplary embodiments, the generation unit 510 may generate a non-linear phantom configured as described with reference to FIG. 3.

In detail, the generation unit 510 may generate a plurality of linear phantoms by mixing the first material and the second material such that thicknesses of the first material and the second material linearly increase or decrease and mixture ratios of the first material and the second material linearly increase or decrease.

In addition, the generation unit 510 may generate a plurality of non-linear phantoms by adding third materials having different thicknesses respectively to the plurality of linear phantoms.

Here, the third materials may include at least one material selected from I, Al, Au, and Ca.

When the generation unit 510 thus generates the non-linear phantoms, the detection unit 520 may detect the phantom information by projecting a multi-energy X-ray on the plurality of non-linear phantoms.

The information generated and stored by the phantom information recording apparatus may be recorded in a DB. The material information detection apparatus of FIG. 1 may detect information on the materials constituting the analysis object, using the information recorded in the DB.

Hereinafter, the material information detection apparatus according to other exemplary embodiments will be described in detail.

Figure 6:
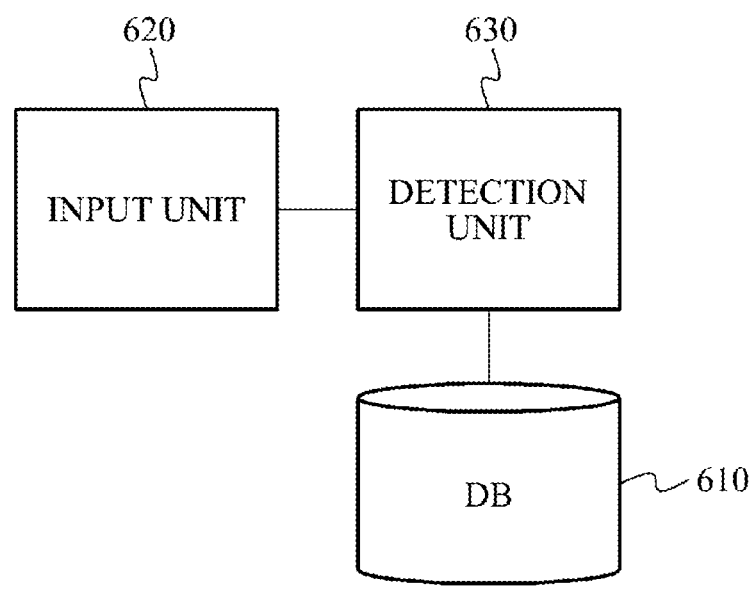
FIG. 6 illustrates a material information detection apparatus according to other exemplary embodiments.

FIG. 6 illustrates a material information detection apparatus according to other exemplary embodiments.

Referring to FIG. 6, the material information detection apparatus may include a database (DB) 610, an input unit (input device) 620, and a detection unit (detector) 630.

The DB 610 may store phantom information obtained by projecting a multi-energy X-ray on a phantom including a plurality of materials. The DB 610 may be generated by the phantom information recording apparatus.

The input unit 620 may receive an input of a plurality of pieces of object information per energy (e.g., per energy level), obtained by projecting a multi-energy X-ray on an analysis object. For example, the input unit 620 may be input with object information obtained by projecting a low-energy X-ray on the analysis object and object information obtained by projecting a high-energy X-ray on the analysis object.

The detection unit 630 may detect information on the materials constituting the analysis object based on the phantom information stored in the DB 610 and the plurality of pieces of object information per energy level. That is, the detection unit 630 may detect the material information such as the thickness, the mixture ratio, and other information of the materials constituting the analysis object, by performing calibration.

The plurality of pieces of object information per energy level may include (1) an object image obtained by projecting a multi-energy X-ray on the object material, and (2) intensity values per energy level with respect to a plurality of pixels of the object image.

The detection unit 630 may detect information on the materials constituting the analysis object using the intensity values per energy level.

In detail, the detection unit 630 may detect a plurality of areas having the intensity values per energy level, from a phantom image obtained by projecting a multi-energy X-ray on the phantom. In addition, the detection unit 630 may detect a crossing area of the plurality of areas. In addition, the detection unit 630 may detect information on at least one selected from (1) a mixture ratio of a plurality of materials constituting a part of the phantom corresponding to the crossing area, and (2) thicknesses of the plurality of materials. The detection unit 630 may use the detected information as the information on the materials constituting the analysis object.

Hereinafter, the operation of detecting the information on the materials constituting the analysis object using the intensity values per energy level by a detection unit of a material information detection apparatus will be described in detail.

Figure 7:
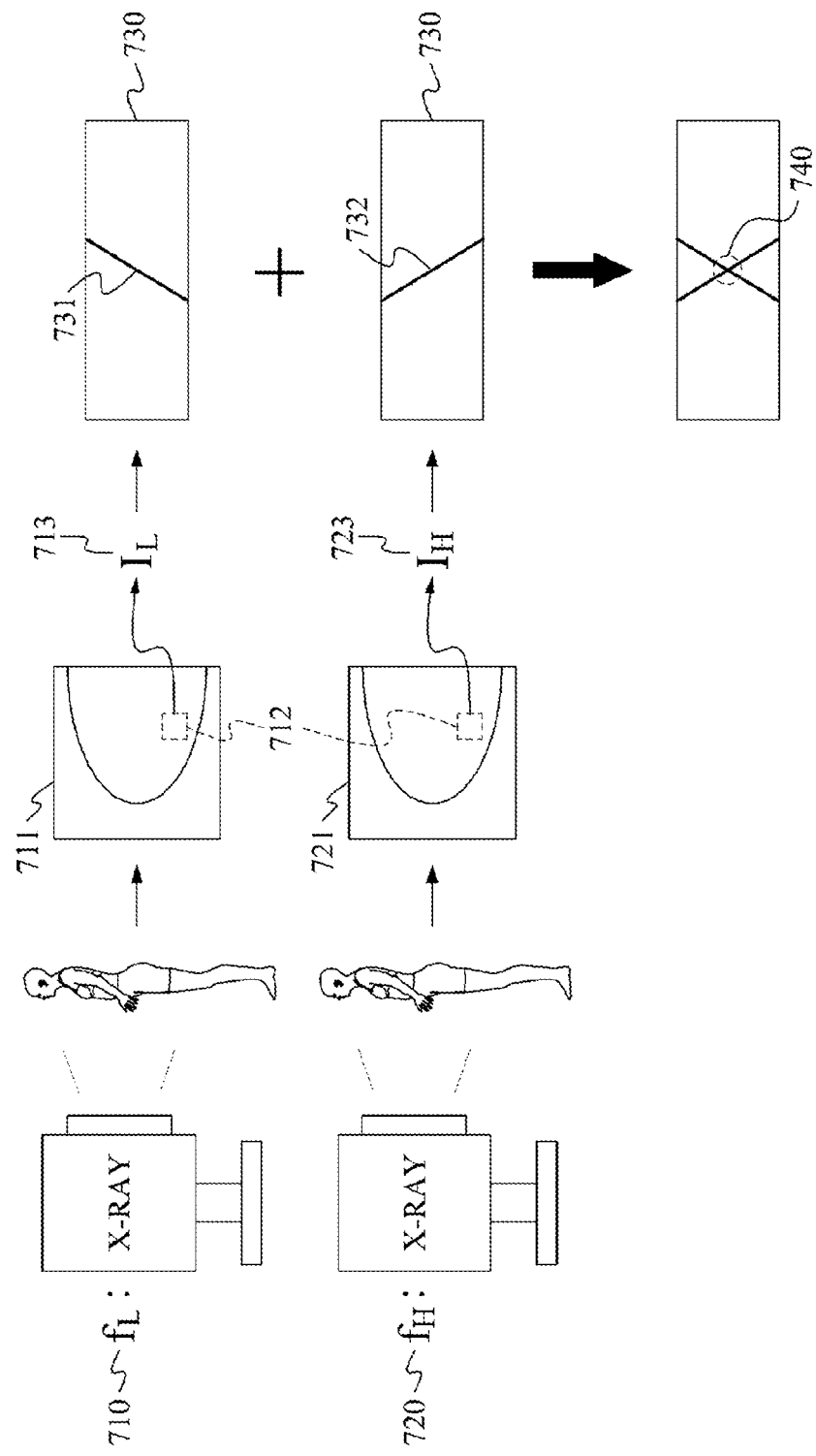
FIG. 7 illustrates an operation of detecting information on materials constituting an analysis object by a detection unit of a material information detection apparatus using intensity values according to energy, according to exemplary embodiments.

FIG. 7 illustrates an operation of detecting the information on materials constituting the analysis object by the detection unit 620 of the material information detection apparatus using intensity values per energy level, according to exemplary embodiments.

Referring to FIG. 7, the plurality of pieces of object information per energy level input by the input unit 620 may include intensity values 713 and 723.

For example, when a low-energy X-ray having a frequency fL 710 is projected on the analysis object, an object image 711 related to a low energy level and a corresponding intensity value per pixel IL 713 may be obtained. Here, for example, the intensity value with respect to a selected pixel 712 from which the information on component materials is to be detected may be set to a value of 10, although it is understood that this value is exemplary only.

When a high-energy X-ray having a frequency fH 720 is projected on the analysis object, an object image 721 related to a high energy level and a corresponding intensity value per pixel IH 723 may be obtained. Here, for example, the intensity value with respect to the selected pixel 712 may be set to a value of 5, although it is understood that this value is exemplary only.

Here, the detection unit 630 may detect areas 731 and 732 having the intensity values per energy level from a phantom image 730 obtained by projecting a multi-energy X-ray on the phantom, so as to detect material information such as information on the materials constituting a part of the analysis object corresponding to the selected pixel 712. For example, the detection unit 630 may detect the area 731 having an intensity value IL at the low energy level, for example 10, from the phantom image 730. In addition, the detection unit 630 may detect the area 732 having an intensity value IH at the high energy level, for example 5, from the phantom image 730.

Also, the detection unit 630 may detect a crossing area 740 of the detected areas per energy level.

The DB 610 may store the phantom image 730 and the information on the materials constituting the part of the phantom corresponding to pixels of the phantom image 730, the information being, for example, a thickness and a mixture ratio. Therefore, by referencing the DB 610, the detection unit 630 may detect information on at least one characteristic selected from (1) a mixture ratio of the plurality of materials constituting the part of the phantom corresponding to the crossing area 740, and (2) thicknesses of the plurality of materials. The detection unit 630 may use the detected information as the information on the materials constituting the analysis object.

For example, when thicknesses of a first material and a second material constituting the part of the phantom corresponding to the crossing area 740 are about 5 cm and a mixture ratio between the first material and the second material is about 5:5, the detection unit 630 may detect the thickness of about 5 cm and the mixture ratio of about 5:5 with respect to the materials constituting the selected pixel of the analysis object, as the information on the materials constituting the analysis object.

Figure 8:
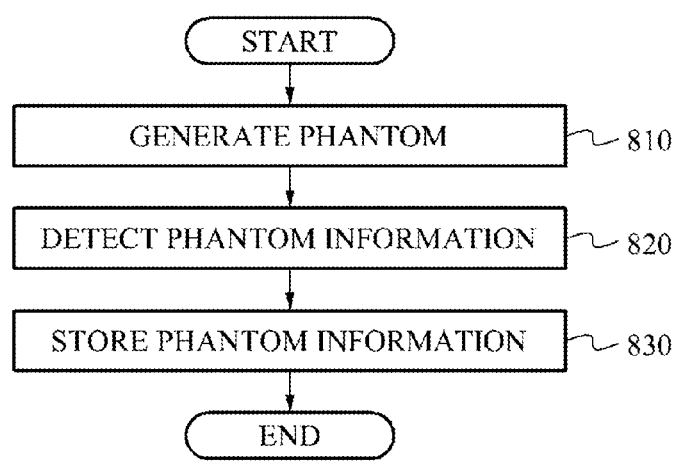
FIG. 8 illustrates an operation method of a phantom information recording apparatus according to exemplary embodiments.

FIG. 8 illustrates an operation method of a phantom information recording apparatus according to exemplary embodiments.

Referring to FIG. 8, in operation 810, the operation method may generate a phantom by mixing a plurality of materials.

In operation 820, the operation method of the phantom information recording apparatus may detect the phantom information by projecting a multi-energy X-ray on the phantom. The phantom information may include a phantom image obtained by photographing the phantom using the multi-energy X-ray and information of component materials, such as a thickness and a mixture ratio, corresponding to positions of pixels of the phantom image.

In operation 830, the operation method of the phantom information recording apparatus may store the phantom information in a DB.

Figure 9:
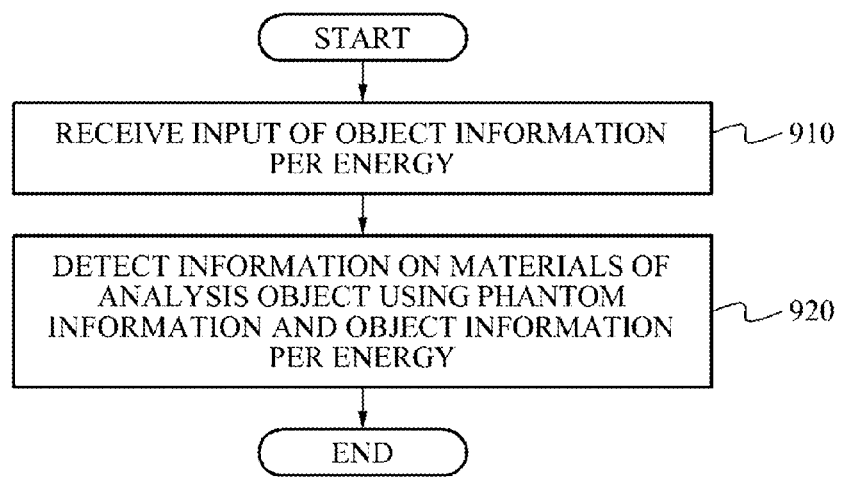
FIG. 9 illustrates an operation method of a material information detection apparatus according to exemplary embodiments.

FIG. 9 illustrates an operation method of a material information detection apparatus according to exemplary embodiments.

Referring to FIG. 9, the operation method of the material information detection apparatus may include receiving an input of a plurality of pieces of object information per energy level, obtained by projecting a multi-energy X-ray on an analysis object, in operation 910. For example, the operation method of the material information detection apparatus may include the material information detection apparatus being input with object information obtained by projecting a low-energy X-ray on the analysis object and object information obtained by projecting a high-energy X-ray on the analysis object.

In operation 920, the operation method of the material information detection apparatus may include detecting information on the materials constituting the analysis object based on the phantom information stored in a DB and the plurality of pieces of object information per energy level. That is, the operation method may include detecting the material information such as the thickness, the mixture ratio, and the like of the materials constituting the analysis object, by performing calibration.

According to an aspect of exemplary embodiments, the plurality of pieces of object information per energy level may include (1) an object image obtained by projecting a multi-energy X-ray on the analysis object, and (2) intensity values per energy level with respect to a plurality of pixels of the object image.

Here, the operation method of the material information detection apparatus may include detecting the information on the materials constituting the analysis object using the intensity values per energy level.

In detail, the operation method may include detecting a plurality of areas having the intensity values per energy level, from a phantom image obtained by projecting a multi-energy X-ray on the phantom. In addition, the operation method may include detecting a crossing area of the plurality of areas. In addition, the detection unit 630 may detect information on at least one characteristic selected from (1) a mixture ratio of a plurality of materials constituting a part of the phantom corresponding to the crossing area, and (2) thicknesses of the plurality of materials. The operation method may include using the detected information as the information on the materials constituting the analysis object.

The units described herein may be implemented using hardware components, software components, or a combination thereof. For example, a processing device used in accordance with the above-described exemplary embodiments may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner.

The processing device may run an operating system (OS) and one or more software applications that run on the OS. The processing device also may access, store, manipulate, process, and create data in response to execution of the software. For purpose of simplicity, the description of a processing device is used in the singular; however, one skilled in the art will appreciate that a processing device may include multiple processing elements and multiple types of processing elements. For example, a processing device may include multiple processors or a processor and a controller. In addition, different processing configurations are possible, such as parallel processors.

The methods according to the above-described exemplary embodiments may be recorded in non-transitory computer-readable media including program instructions to implement various operations which may be performed by a computer. The media may also include, alone or in combination with the program instructions, data files, data structures, and the like. The program instructions recorded on the media may be those specially designed and constructed for the purposes of the exemplary embodiments, or they may be of the well-known kind and available to those having skill in the computer software arts. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The media may be transfer media such as optical lines, metal lines, or waveguides including a carrier wave for transmitting a signal designating the program command and the data construction. Examples of program instructions include both machine code, such as code produced by a compiler, and files containing higher level code that may be executed by the computer using an interpreter. The described hardware devices may be configured to act as one or more software modules in order to perform the operations of the above-described exemplary embodiments, or vice versa.

Although exemplary embodiments have been shown and described, it would be appreciated by those skilled in the art that changes may be made in these exemplary embodiments without departing from the principles and spirit of the disclosure, the scope of which is defined in the claims and their equivalents.

What is claimed is:

1. A material information detection apparatus comprising:
   a database configured to store phantom information obtained by projecting a multi-energy X-ray on a phantom comprising a plurality of materials;
   an input device configured to receive a plurality of pieces of object information per energy level, the object information obtained by projecting a multi-energy X-ray on an analysis object; and
   a detector configured to detect information related to materials constituting the analysis object based on the phantom information and the plurality of pieces of object information per energy level.

2. The material information detection apparatus of claim 1, wherein the phantom comprises:
   a linear phantom configured such that thicknesses of a plurality of materials constituting the linear phantom linearly increase or decrease and mixture ratios of the plurality of materials constituting the linear phantom linearly increase or decrease; and
   a non-linear phantom configured such that thickness of at least one material of a plurality of materials constituting the non-linear phantom non-linearly increases or decreases, or a mixture ratio of at least one material of the plurality of materials constituting the non-linear phantom non-linearly increases or decreases.

3. The material information detection apparatus of claim 1, wherein the plurality of pieces of object information per energy level comprises an object image obtained by projecting a multi-energy X-ray on the analysis object, and intensity values per energy level with respect to a plurality of pixels of the object image.

4. The material information detection apparatus of claim 3, wherein
   the phantom information comprises a phantom image obtained by projecting the multi-energy X-ray on the phantom,
   the detector performs the operations of:
   detecting a plurality of areas having the intensity values per energy level from the phantom image;
   detecting a crossing area of the plurality of areas;
   detecting at least one type of information selected from (1) mixture ratios of the plurality of materials constituting a part of the phantom corresponding to the crossing area, and (2) thicknesses of the plurality of materials; and
   using the at least one type of information as the information related to the materials constituting the analysis object.

5. A phantom information recording apparatus comprising:
   a generator configured to generate a phantom by mixing a plurality of materials;
   a detector configured to detect phantom information by projecting a multi-energy X-ray on the phantom; and
   a storage configured to store the phantom information.

6. The phantom information recording apparatus of claim 5, wherein
   the generator performs the operations of:
   generating a first linear phantom by mixing a first material and a second material such that thicknesses of the first material and the second material linearly increase or decrease and such that mixture ratios of the first material and the second material linearly increase or decrease; and
   generating a second linear phantom by mixing a third material and a fourth material such that thicknesses of the third material and the fourth material linearly increase or decrease and such that mixture ratios of the third material and the fourth material linearly increase or decrease, and
   the detector detects the phantom information by projecting a multi-energy X-ray on the first linear phantom and the second linear phantom.

7. The phantom information recording apparatus of claim 6, wherein the first material, the second material, the third material, and the fourth material comprise at least one material selected from an adipose tissue and a glandular tissue.

8. The phantom information recording apparatus of claim 5, wherein
the generator performs the operations of:
generating a plurality of first linear phantoms by mixing a first material and a second material such that thicknesses of the first material and the second material linearly increase or decrease and such that mixture ratios of the first material and the second material linearly increase or decrease; and
generating a plurality of non-linear phantoms by adding third materials having different thicknesses to the plurality of linear phantoms, and
the detector detects the phantom information by projecting a multi-energy X-ray on the plurality of non-linear phantoms.

9. The phantom information recording apparatus of claim 8, wherein the third materials each comprise at least one selected from iodine (I), aluminum (Al), gold (Au), and calcium (Ca).

10. A method to be performed by a material information detection apparatus, the operation method comprising:
receiving a plurality of pieces of object information per energy level, the object information obtained by projecting a multi-energy X-ray on an analysis object; and
detecting information related to materials constituting the analysis object based on phantom information and the plurality of pieces of object information per energy level, the phantom information being stored in a database of the material information detection apparatus,
wherein the phantom information is information obtained by projecting the multi-energy X-ray on a phantom comprising a plurality of materials.

11. The operation method of claim 10, wherein the plurality of pieces of object information per energy level comprises an object image obtained by projecting a multi-energy X-ray on the analysis object, and an intensity value per energy level with respect to a plurality of pixels of the object image.

12. The operation method of claim 11, wherein
the phantom information comprises a phantom image obtained by projecting a multi-energy X-ray on the phantom, and
the detecting of the information related to the materials constituting the analysis object comprises:
detecting a plurality of areas having the intensity value per energy level from the phantom image;
detecting a crossing area of the plurality of areas;
detecting at least one type of information selected from (1) mixture ratios of the plurality of materials constituting a part of the phantom corresponding to the crossing area, and (2) thicknesses of the plurality of materials; and
using the at least one type of information as the information related to the materials constituting the analysis object.

13. A method to be performed by a phantom information recoding apparatus, the method comprising:
generating a phantom by mixing a plurality of materials;
detecting phantom information by projecting a multi-energy X-ray on the phantom; and
storing the phantom information.

14. A non-transitory computer readable recording medium storing a program which causes a computer to perform a method comprising:
receiving a plurality of pieces of object information per energy level, the object information obtained by projecting a multi-energy X-ray on an analysis object; and
detecting information related to materials constituting the analysis object based on phantom information and the plurality of pieces of object information per energy level, the phantom information being stored in a database of a material information detection apparatus,
wherein the phantom information is information obtained by projecting the multi-energy X-ray on a phantom comprising a plurality of materials.

15. A device to detect phantom information, the device comprising:
a phantom comprising a first material, a second material, and a third material, the first and second materials being mixed with each other to form a mixture, the mixture being disposed on top of the third material; and
a detector configured to detect the phantom information by projecting an X-ray on the phantom,
wherein the mixture has a linearly increasing thickness in a direction moving from a first surface of the phantom towards a second surface of the phantom opposite the first surface, and the third material has a constant thickness along the direction.

16. The device according to claim 15, wherein the mixture has a mixture ratio which linearly changes in a direction moving from a third surface of the phantom towards a fourth surface of the phantom opposite the third surface, and the third material has a constant mixture ratio.

17. The device according to claim 15, wherein the detector projects an X-ray comprising multiple energy levels onto the phantom.

18. The device according to claim 15, further comprising a storage to store the phantom information.

19. The device according to claim 15, wherein the third material comprises at least one selected from iodine (I), aluminum (Al), gold (Au), and calcium (Ca).

20. The device according to claim 15, wherein the mixture is formed as a trapezoidal shape, and the third material is formed in a rectangular shape.

* * * * *